US010687953B2

United States Patent
Lam et al.

(10) Patent No.: US 10,687,953 B2
(45) Date of Patent: Jun. 23, 2020

(54) APPARATUSES AND METHODS FOR ANTERIOR CERVICAL TRANSARTICULAR FIXATION

(71) Applicants: Kenrick Chur-wei Lam, Galveston, TX (US); Sohum Desai, Galveston, TX (US); Daniel Williams Branch, Dickinson, TX (US)

(72) Inventors: Kenrick Chur-wei Lam, Galveston, TX (US); Sohum Desai, Galveston, TX (US); Daniel Williams Branch, Dickinson, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 255 days.

(21) Appl. No.: 15/898,860

(22) Filed: Feb. 19, 2018

(65) Prior Publication Data

US 2018/0235766 A1 Aug. 23, 2018

Related U.S. Application Data

(60) Provisional application No. 62/460,220, filed on Feb. 17, 2017.

(51) Int. Cl.
*A61B 17/80* (2006.01)
*A61B 17/70* (2006.01)
*A61F 2/44* (2006.01)
*A61F 2/46* (2006.01)
*A61B 17/86* (2006.01)

(52) U.S. Cl.
CPC .............. *A61F 2/44* (2013.01); *A61B 17/70* (2013.01); *A61B 17/7059* (2013.01); *A61B 17/8033* (2013.01); *A61B 17/86* (2013.01); *A61F 2/4611* (2013.01); *A61B 2017/8655* (2013.01)

(58) Field of Classification Search
CPC ........................ A61B 17/7059; A61B 17/8033
See application file for complete search history.

(56) References Cited

U.S. PATENT DOCUMENTS

| 3,741,205 | A | * | 6/1973 | Markolf | ............. | A61B 17/7059 606/291 |
| 5,318,567 | A | * | 6/1994 | Vichard | ............. | A61B 17/8061 606/286 |
| 6,224,602 | B1 | | 5/2001 | Hayes | | |
| 6,379,354 | B1 | | 4/2002 | Rogozinski | | |
| 7,468,069 | B2 | | 12/2008 | Baynham | | |

(Continued)

OTHER PUBLICATIONS

Kerschbaumer, et al., "Transoral decompression, anterior plate fixation, and posterior wire fusion for Irreducible Atlantoaxial kyphosis in rheumatoid arthritis", SPINE vol. 25, No. 20, 2000.

(Continued)

*Primary Examiner* — Nicholas W Woodall
(74) *Attorney, Agent, or Firm* — Thomas | Horstemeyer, LLP

(57) ABSTRACT

In one embodiment, an anterior cervical transarticular fixation implant including a cervical plate including a central body, lateral wings that extend laterally outward from the central body, each lateral wing including a fastener opening configured to receive a fastener configured to thread into vertebrae, and locking mechanisms configured to selectively lock the fasteners in place.

20 Claims, 4 Drawing Sheets

(56) References Cited

U.S. PATENT DOCUMENTS

| | | | |
|---|---|---|---|
| 9,788,874 B2* | 10/2017 | Clasbrummel | A61B 17/8052 |
| 2008/0281326 A1* | 11/2008 | Watanabe | A61B 17/164 |
| | | | 606/62 |
| 2009/0287258 A1* | 11/2009 | Vannemreddy | A61B 17/7059 |
| | | | 606/298 |
| 2010/0268230 A1* | 10/2010 | Hart | A61B 17/7059 |
| | | | 606/70 |
| 2012/0078305 A1* | 3/2012 | Wang | A61B 17/7059 |
| | | | 606/257 |
| 2014/0172025 A1* | 6/2014 | Vaughan | A61B 17/1757 |
| | | | 606/309 |
| 2016/0296259 A1* | 10/2016 | Lee | A61B 17/7071 |
| 2017/0156764 A1* | 6/2017 | Squires | A61B 17/7071 |

OTHER PUBLICATIONS

Kim, et al., "Biomechanical comparison of anterior and posterior stabilization methods in atlantoaxial instability", J. Neurosurg (Spine 3) 100, 2004.

Koller, et al., "Anterior retropharyngeal fixation C1-2 for stabilization of atlantozxial instabilities: study of feasiblity, technical description and preliminary results", Eur Spine J 15, 2006.

Platzer, et al., "Plate fixation of odontoid fractures without C1-C2 arthrodesis: practice of a novel surgical technique for stabilization of odontoid fractures, including the opportunity to extend the fixation to C3", Clinical studies, vol. 64, No. 4, Apr. 2009.

Reindl, et al., "Anterior instrumentation for traumatic C1-C2 Instability", Spine vol. 28, No. 17, 2003.

Cai, et al., "Evaluation of biomechanical properties of anterior atlantoaxial transarticular locking plate system using three-dimensional finite element analysis", Eur Spine J., 2013.

\* cited by examiner

APPARATUSES AND METHODS FOR ANTERIOR CERVICAL TRANSARTICULAR FIXATION

CROSS-REFERENCE TO RELATED APPLICATION

This application claims priority to U.S. Provisional Application Ser. No. 62/460,220, filed Feb. 17, 2017, which is hereby incorporated by reference herein in its entirety.

BACKGROUND

Odontoid fractures are becoming more prevalent as the population ages. Both nonoperative and external fixation of geriatric odontoid fractures are associated with a high rate of non-union or poor outcome. Furthermore, recent data from an AOSpine North America study group support operative intervention in the elderly.

There are numerous options for internal fixation of odontoid fractures. These options include posteriorly based approaches and anteriorly based approaches. Posterior approaches include C1-C2 transarticular screws, posterior sublaminar wiring, and the use of C1 lateral mass screws with either a C2 pedicle, pars, or translaminar screws. Unfortunately, there are disadvantages of posterior fixation in the elderly, including the loss of joint motion and poor wound healing.

Anterior approaches include fixation using odontoid screws in which a single lag screw is inserted across the fracture line at the base of the dens using a standard Smith-Robinson approach. Such a procedure provides several advantages over posterior approaches. For example, this anterior approach is minimally invasive, motion preserving, and tends to have better wound-healing profiles than posterior approaches. However, fixation using a single odontoid screw is not suitable for every case, especially with patients with anterior oblique fractures, those having injury to the transverse and alar ligaments, or those with an unfavorable body habitus.

Another anterior approach that has been described in the literature is a transoral approach in which access to the vertebrae is achieved by making an incision in the posterior of the pharynx. In this approach, anterior C1-C2 transarticular screws are inserted either with or without a Harm's plate. Biomechanical testing has demonstrated that the procedures using a Harm's plate were inferior to all of the above-mentioned techniques. Although standalone anterior C1-C2 transarticular screws were observed to be noninferior to posterior C1-C2 transarticular screws, the transoral approach is unattractive as there are risks of contamination from exposure to bacteria within the mouth and pharynx.

In view of the above discussion, it can be appreciated that it would be desirable to have apparatuses and methods for achieving effective anterior cervical transarticular fixation that do not require a transoral approach.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
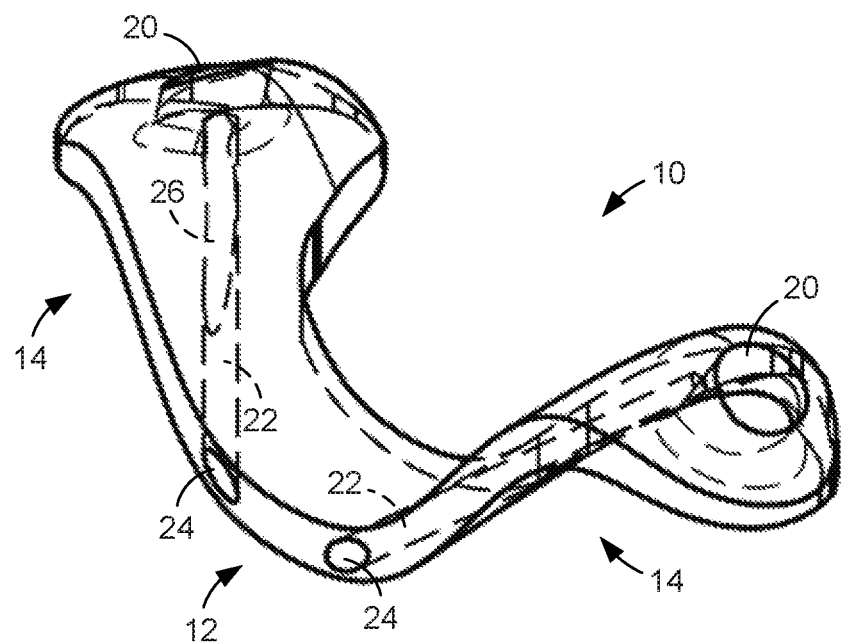
FIG. 1 is a first perspective view of an embodiment of an implantable cervical plate configured for C1-C2 transarticular fixation.
Figure 2:
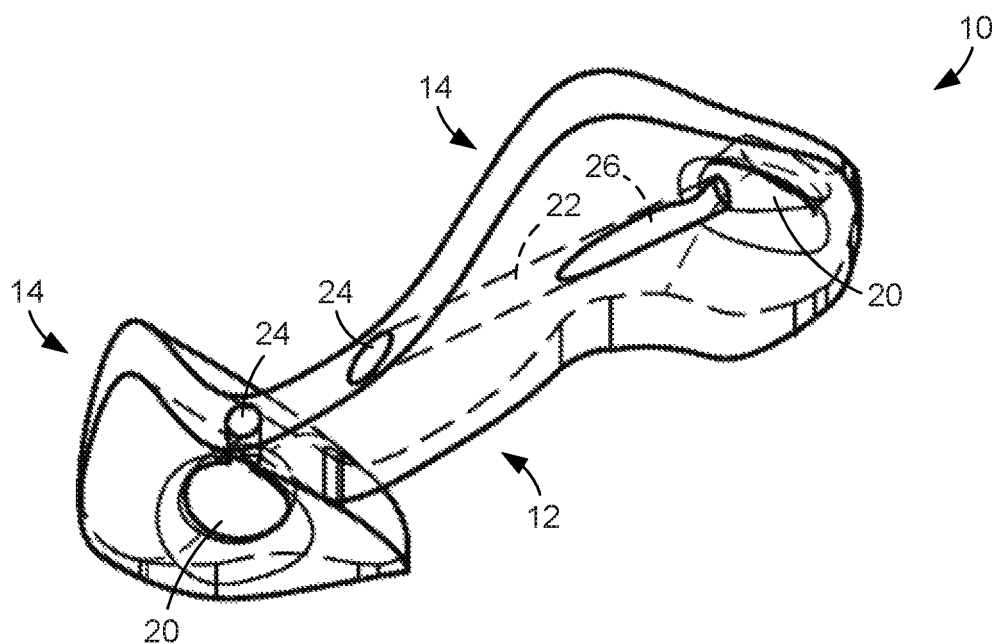
FIG. 2 is a second perspective view of the cervical plate of FIG. 1.

As described above, it would be desirable to have apparatuses and methods for achieving effective anterior cervical transarticular fixation that do not require a transoral approach. Disclosed herein are examples of such apparatuses and methods. The apparatuses comprise anterior cervical transarticular fixation implants that include an implantable cervical plate configured for anterior C1-C2 transarticular fixation. In some embodiments, the cervical plate includes lateral wings that each comprise an opening through which a fastener, such as a transarticular screw, can be passed and locking mechanisms that are configured to prevent rotation of the fasteners after they have been threaded into place within the C1 and C2 vertebrae. In some embodiments, the locking mechanisms each comprise a locking pin that is threaded into a passage that extends through the cervical plate the same general direction as the direction along which the associated fastener extends. The locking pins each have an engagement surface that can be made to positively engage the head of its associated fastener when the pin is threaded into its passage.

The disclosed apparatus can be implanted using the Smith-Robinson technique to expose the atlantoaxial joints and thereby avoid contamination of the field with oral flora. The configurations of the cervical plate and its locking mechanisms facilitate implantation by the surgeon while working within a small space. The disclosed apparatus is particularly useful for geriatric odontoid fractures that are not amenable to odontoid screws as the apparatus can be implanted using an anterior approach, which has a complication profile that is superior to those of posterior approaches.

In the following disclosure, various specific embodiments are described. It is to be understood that those embodiments are example implementations of the disclosed inventions and that alternative embodiments are possible. All such embodiments are intended to fall within the scope of this disclosure.

FIGS. 1-5 illustrate an embodiment of an implantable cervical plate 10 of an anterior cervical transarticular fixation implant that is configured for C1-C2 transarticular fixation. As is apparent in these figures, the cervical plate 10 is constructed from a single, unitary piece of material. The material comprises a rigid biocompatible material, such as stainless steel or a titanium alloy. The cervical plate 10 generally includes a central body 12 from which extends lateral wings 14. As can be appreciated from the figures, both the central body 12 and the wings are curved so as to fit the contours of the anterior side of the C2 vertebra. As is most clearly illustrated in the bottom view of FIG. 4, the central body 12 has a convex curvature in which, when the cervical plate 10 is implanted, the center of the body extends farthest forward (upward in the orientation of FIG. 4) in the anterior direction and the lateral portions of the body extend backward (downward in the orientation of FIG. 4) in the posterior direction.

Figure 4:
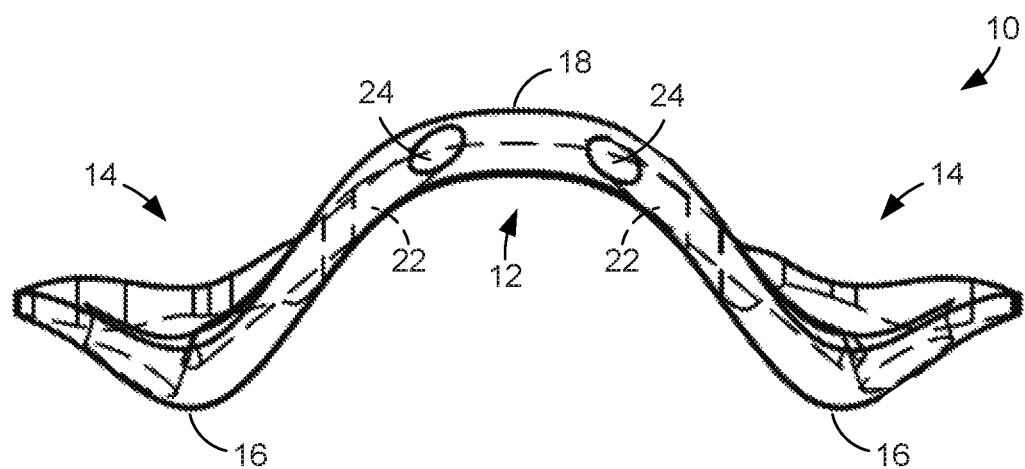
FIG. 4 is a bottom view of the cervical plate of FIG. 1.
Figure 5:
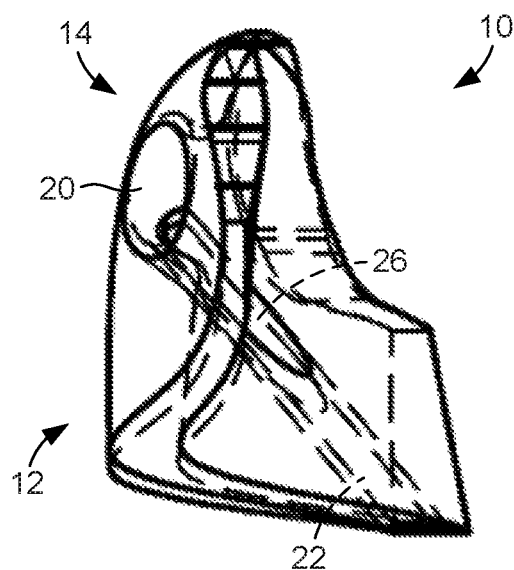
FIG. 5 is a side view of the cervical plate of FIG. 1.

With further reference to FIG. 4, the curvature of the central body 12 continues into the lateral wings 14, which each extend backward until inflection points 16, at which they reverse direction and curve forward in the anterior direction (upward in the orientation of FIG. 4). The lateral wings 14 then curve outwardly in the lateral direction such that the tip portions of the wings generally lie within a frontal plane. As can be seen in FIG. 4, the above-described curvatures result in a generally sinusoidal wave shape (as the cervical plate 10 is viewed from below) in which, as the plate is traversed from lateral tip to lateral tip, the wave drops to a first trough at the inflection point 16, rises to a peak 18 at the central body 12, drops to a second trough at the other inflection point 16, and then rises from the second trough.

Figure 3:
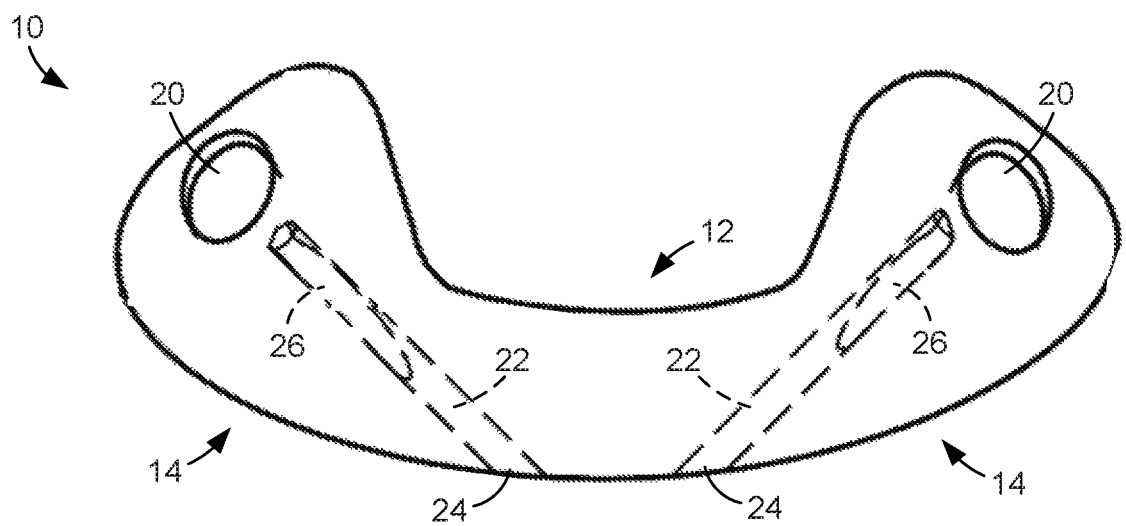
FIG. 3 is a front view of the cervical plate of FIG. 1.

With reference to the front view of FIG. 3, the central body 12 can be short in height relative to the lateral wings 14, and the lateral wings can not only extend laterally but also extend upwardly such that the cervical plate 10 has a U-shape when viewed from the front (or rear). As is shown most clearly in FIG. 3, a fastener opening 20 is provided within each wing 14 near its upper lateral tip and the inflection points 16 (see FIG. 4). These openings 20 are configured to receive fasteners, such as transarticular screws (see FIG. 7), that can be threaded into a patient's C2 and C1 vertebrae during a fixation procedure. In some embodiments, these fasteners can be variable-angle transarticular screws that enable a surgeon to vary the angle at which the screws thread into the vertebrae. In some embodiments, such variable-angle transarticular screws have rounded heads that enable this variance and the openings 20 can be countersunk to receive the rounded portions of the heads. Irrespective of the nature of the fasteners, they are driven through the vertebrae in a posterior, upward direction, as described below.

As is also shown in FIG. 3, threaded pin passages 22 are formed within the cervical plate 10. These passages 22, along with locking pins described below, form part of the locking mechanisms that secure the fasteners in place. As shown in FIG. 3, the passages 22 extend from first, lower, generally circular openings 24 formed in the bottom of the central body 12 and extend laterally, posteriorly, and upwardly through the lateral wings 14 toward the fastener openings 20 and terminate in second, upper, elongated elliptical openings 26 that open to the fastener openings. These passages 22 are configured to receive locking pins whose proximal heads are accessible to the surgeon through the lower openings 24 and whose distal tips extend from the upper openings 26 to engage the fasteners when they have passed through the fastener openings 20.

Figures 6A, 6B:
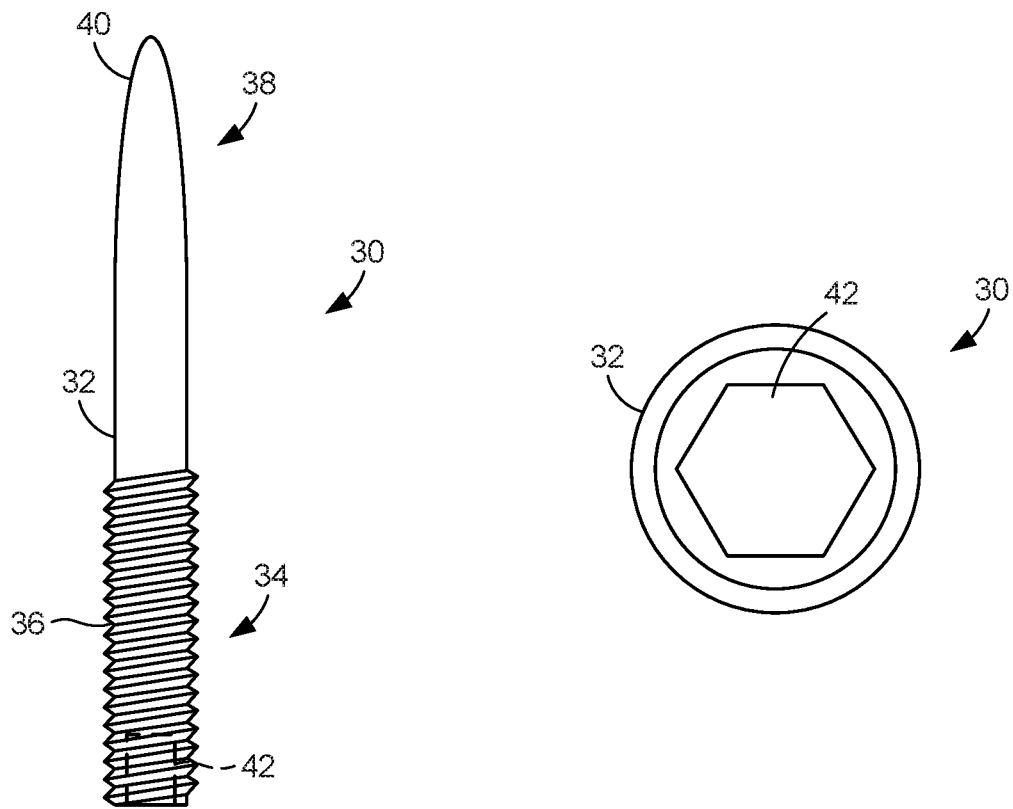
FIG. 6A is a side view of an embodiment of a locking pin that can be used with the cervical plate of FIG. 1.
FIG. 6B is an end view of the locking pin of FIG. 6A.

FIGS. 6A and 6B illustrate an example embodiment for the locking pins 30. As shown in these figures, each locking pin 30 comprises an elongated shaft 32. A proximal portion 34 of the shaft 32 includes threads 36 that are configured to mate with similar threads provided within a threaded pin passage 22. A distal portion 38 of the shaft 32 includes a rounded conical tip 40 that is configured to engage the head of an associated fastener (e.g., transarticular screw). As shown most clearly in FIG. 6B, a hexagonal cavity 42 is formed at the proximal end of the shaft 32. This cavity 42 is configured to receive a hexagonal key or wrench that can be used to thread the pin 30 through its pin passage 24 and to urge the conical tip 40 into firm contact with the associated fastener head.

It is noted that both the fasteners and the pins 30 extend posteriorly and upwardly when the cervical plate 10 is implanted. Accordingly, the fastener heads and the pin heads are each accessible to the surgeon from the anterior side of the cervical plate 10, and along the same line of sight. This facilitates and greatly simplifies the fixation procedure for the surgeon. Significantly, this is different from conventional fixation plates in which the locking mechanisms extend in and are approached from a direction that is generally perpendicular to the direction along which the fasteners extend.

Figure 7:
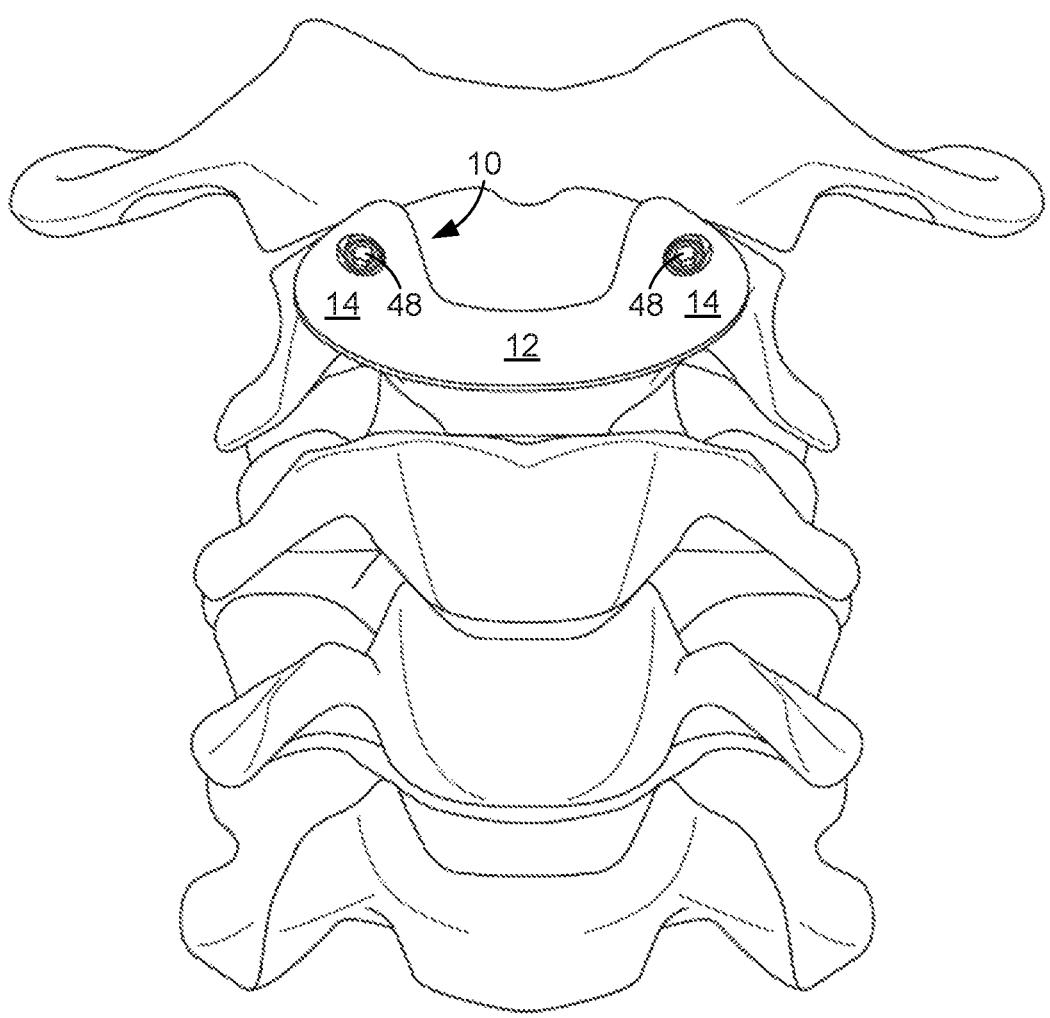
FIG. 7 is an anterior view of the cervical portion of the spine with the cervical plate of FIG. 1 shown secured to the C2 and C1 vertebrae.

During a fixation procedure, a Smith-Robinson incision is made in the patient's neck. Once access to the spine has been achieved, the cervical plate 10 is applied to the anterior of the C2 vertebrae and pilot holes are drilled through the fastener openings 20 and into the lateral masses of the C2 and C1 vertebrae to establish paths for the fasteners. These holes are formed in the posterior and upward direction through the vertebrae. Once the pilot holes have been drilled, the fasteners, such as transarticular screws, are passed through the fastener openings 20 and are threaded into the vertebrae to affix the vertebrae together along the posterior and upward directions of the pilot holes. This fixation is illustrated in FIG. 7, which shows the cervical plate 10 affixed to the spine with transarticular screws 48. As can be appreciated from this figure, the screws 48 have been threaded posteriorly and upwardly through the lateral masses of the C2 vertebra and into the lateral masses of the C1 vertebra so as to affix the two vertebrae together.

After the fasteners (e.g., screws 48) have been fully threaded into the vertebrae and properly seated within the fastener openings 20, the fasteners can be selectively locked in place to prevent them from loosening. This is achieved using the locking pins 30. Specifically, the locking pins 30 are threaded into the pin passages 22 until the conical tips 40 of the pins firmly engage the proximal ends of the heads of the associated fasteners. This engagement prevents the fasteners from backing out of the vertebrae and, therefore, locks the fasteners in place. As mentioned above, the surgeon can approach and manipulate both the fasteners and the locking pins 30 from the same (anterior) side of the cervical plate 10 and the same general direction. This enables the procedure to be performed more easily and with less disruption of the patient's tissues.

The invention claimed is:

1. An anterior cervical transarticular fixation implant for fixation of the C1 and C2 vertebrae of a patient, the implant comprising:
   a cervical plate including:
      a central body,
      lateral wings that extend laterally outward from the central body, each lateral wing including a fastener opening configured to receive a fastener configured to thread into vertebrae, and
      locking mechanisms configured to selectively lock the fasteners in place;
      wherein the central body and the lateral wings are curved in a manner in which the cervical plate is configured to fit the contours of the anterior side of the C2 vertebra;
      wherein the fastener openings extend posteriorly and upwardly through the cervical plate such that, when the cervical plate is applied to the C2 vertebra, fasteners passed through the fastener openings are directed through C2 vertebra and into the C1 vertebra.

2. The implant of claim 1, wherein the central body and the lateral wings of the cervical plate are unitarily formed from a single piece of material.

3. The implant of claim 1, wherein the cervical plate includes two lateral wings, the wings extending in opposite lateral directions.

4. The implant of claim 1, wherein the fastener openings of the cervical plate are countersunk.

5. The implant of claim 1, wherein the locking mechanisms comprise locking pins that can selectively engage the fasteners.

6. The implant of claim 5, wherein the locking pins are threaded and the cervical plate further includes threaded pin passages through which the locking pins pass.

7. The implant of claim 6, wherein the locking pins each comprise an elongated shaft having a proximal portion and a distal portion, the proximal portion including threads configured to engage threads of the associated threaded pin passage and the distal portion including a rounded conical tip configured to engage the associated fastener.

8. The implant of claim 7, wherein the threaded pin passages extend through the central body and the lateral wings of the cervical plate.

9. The implant of claim 8, wherein each threaded pin passage extends from a first opening formed in the bottom of the central body of the cervical plate to a second opening formed adjacent to one of the fastener openings of the cervical plate.

10. The implant of claim 9, wherein the passages extend laterally, posteriorly, and upwardly through the cervical plate so as to be angled relative to the vertical and horizontal directions.

11. The implant of claim 1, wherein the central body and the lateral wings of the cervical plate are curved.

12. The implant of claim 11, wherein the central body and lateral wings of the cervical plate are curved in a manner in which the cervical plate has a sinusoidal wave shape when viewed from the bottom.

13. The implant of claim 1, wherein the cervical plate has a U-shape when viewed from the front.

14. The implant of claim 13, wherein the central body forms a generally horizontal center portion of the U-shape and the lateral wings form generally vertical side portions of the U-shape.

15. The implant of claim 1, further comprising threaded fasteners configured to pass through the fastener openings and thread into the vertebrae.

16. The implant of claim 15, wherein the threaded fasteners are transarticular screws.

17. A method for performing anterior cervical transarticular fixation, the method comprising:
    making a Smith-Robinson incision in the neck of a patient;
    applying a curved cervical plate to the anterior of the C2 vertebrae;
    drilling pilot holes through fastener openings in the cervical plate, through the C2 vertebra, and into the C1 vertebra, the holes traversing a posterior and upward direction through the vertebrae;
    passing threaded fasteners through the fastener openings and threading them into the C2 and C1 vertebrae along the directions of the pilot holes; and
    locking the threaded fasteners in place with locking mechanisms integrated into the cervical plate.

18. The method of claim 17, wherein locking the transarticular screws comprises engaging heads of the threaded fasteners with locking pins that prevent the threaded fasteners from backing out of the vertebrae.

19. The method of claim 18, wherein engaging heads of the threaded fasteners with locking pins comprises threading the locking pins through threaded pin passages that extend through the cervical plate.

20. The method of claim 19, wherein threading the locking pins through threaded pin passages comprises accessing the locking pins from first openings formed in a bottom of a central body of the cervical plate and rotating the locking pins within the pin passages until tips of the pins engage the fastener heads.

\* \* \* \* \*